US012622619B2

(12) United States Patent
Yan et al.

(10) Patent No.: US 12,622,619 B2
(45) Date of Patent: May 12, 2026

(54) DRIVER ATTENTION MONITORING

(71) Applicant: INTERNATIONAL BUSINESS MACHINES CORPORATION, Armonk, NY (US)

(72) Inventors: Zhe Yan, Beijing (CN); Li Li Guan, Beijing (CN); Rong Zhao, Beijing (CN); Li Bo Zhang, Beijing (CN); Hao Xiang Wu, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 44 days.

(21) Appl. No.: 18/738,546

(22) Filed: Jun. 10, 2024

(65) Prior Publication Data

US 2025/0375131 A1 Dec. 11, 2025

(51) Int. Cl.

| | |
|---|---|
| ***A61B 5/18*** | (2006.01) |
| ***A61B 5/00*** | (2006.01) |
| ***B60Q 9/00*** | (2006.01) |
| ***G06Q 10/0639*** | (2023.01) |
| *G06F 40/35* | (2020.01) |

(52) U.S. Cl.

CPC .............. *A61B 5/18* (2013.01); *A61B 5/4803* (2013.01); *A61B 5/6893* (2013.01); *A61B 5/7278* (2013.01); *A61B 5/7465* (2013.01); *B60Q 9/00* (2013.01); *G06Q 10/06398* (2013.01); *G06F 40/35* (2020.01)

(58) Field of Classification Search

CPC ....... A61B 5/18; A61B 5/4803; A61B 5/6893; A61B 5/7278; A61B 5/7465; B60Q 9/00; G06Q 10/06398; G06F 40/35

USPC .......................................................... 340/439

See application file for complete search history.

(56) References Cited

U.S. PATENT DOCUMENTS

| | | | | |
|---|---|---|---|---|
| 8,384,534 B2 * | 2/2013 | James | .................. | B60W 50/14<br>342/107 |
| 10,157,423 B1 * | 12/2018 | Fields | ................. | B60W 50/082 |
| 10,482,333 B1 * | 11/2019 | el Kaliouby | ........... | G16H 20/70 |

(Continued)

FOREIGN PATENT DOCUMENTS

| | | |
|---|---|---|
| CN | 114495495 A | 5/2022 |
| CN | 115140065 A | 10/2022 |

(Continued)

OTHER PUBLICATIONS

Baldwin et al., "Detecting and Quantifying Mind Wandering during Simulated Driving", Frontiers in Human Neuroscience, Aug. 8, 2017, vol. 11, Article 406, 15 pages, <https://www.frontiersin.org/articles/10.3389/fnhum.2017.00406/full>.

(Continued)

*Primary Examiner* — Zhen Y Wu
(74) *Attorney, Agent, or Firm* — Kristofer Haggerty

(57) ABSTRACT

Disclosed are a computer-implemented method, a system and a computer program product for monitoring driver attention. A traffic event occurring during a driving task of a driver on a road can be monitored. A behavior of the driver in response to the traffic event can be detected. An attention level of the driver can be determined at least based on a match of the detected behavior of the driver with an expected behavior in response to the traffic event. Accordingly, the attention level of the driver can be reliably predicted and the driver distraction can be efficiently prevented, thereby improving the driving safety.

19 Claims, 11 Drawing Sheets

(56) References Cited

U.S. PATENT DOCUMENTS

| | | | | |
|---|---|---|---|---|
| 11,299,174 | B2 * | 4/2022 | Boss | A61B 5/168 |
| 11,352,013 | B1 | 6/2022 | Srinivasan | |
| 11,498,581 | B1 * | 11/2022 | Forster | B60W 50/10 |
| 12,330,557 | B2 * | 6/2025 | Ye | G07C 5/02 |
| 2003/0236605 | A1 * | 12/2003 | Takahashi | B60T 7/22<br>348/148 |
| 2010/0102972 | A1 | 4/2010 | Middlekauff | |
| 2017/0297564 | A1 * | 10/2017 | Xi | B60W 30/18145 |
| 2018/0053102 | A1 * | 2/2018 | Martinson | G08G 1/09623 |
| 2018/0330178 | A1 * | 11/2018 | el Kaliouby | A61B 5/6893 |
| 2019/0143994 | A1 * | 5/2019 | Chen | G06N 5/046<br>340/576 |
| 2019/0152492 | A1 * | 5/2019 | el Kaliouby | G06V 10/82 |
| 2019/0213429 | A1 * | 7/2019 | Sicconi | G06V 40/18 |
| 2020/0156654 | A1 * | 5/2020 | Boss | A61B 5/12 |
| 2020/0342868 | A1 * | 10/2020 | Lou | G10L 15/22 |
| 2021/0174103 | A1 * | 6/2021 | Schumacher | G06F 18/22 |
| 2021/0291870 | A1 * | 9/2021 | Hutchings | B60W 40/08 |
| 2024/0198904 | A1 * | 6/2024 | Ye | G07C 5/02 |

FOREIGN PATENT DOCUMENTS

| | | | |
|---|---|---|---|
| CN | 115339460 | A | 11/2022 |
| CN | 111688710 | B | 6/2023 |

OTHER PUBLICATIONS

Kotseruba et al., "Behavioral Research and Practical Models of Drivers' Attention," arXiv:2104.05677v3 [cs.CV], Dec. 13, 2021, 78 pages, <https://arxiv.org/abs/2104.05677>.

Liu et al., "Impact of Visual Distraction Level on Driving Behavior in Different Traffic Environments," Journal of Highway and Transportation Research and Development, May 2023, pp. 178-183, vol. 40 Issue 5, DOI: 10.3969/j.issn.1002-0268.2023.05.024, English Abstract Only, <http://www.gljtkj.com/CN/10.3969/j.issn.1002-0268.2023.05.024>.

* cited by examiner

400

Driving environment: 501
- Speed limit: 80km/h
- 3 lanes, at the 3th lane
- Car in the left lane
- ...

Trigger condition: 502
- Exceed speed limit (90km/h)

Question type: 503
- Special question

LLM 500

Question: 504
- Speed is too high, why?

Possible Answers :
- I need to go fast.
- I want to overtake the car.
- I'm going to be late!
- Sorry, I don't know the speed limit.
- ...

1000

S1001 MONITORING A TRAFFIC EVENT OCCURRING DURING A DRIVING TASK OF A DRIVER ON A ROAD

S1002 DETECTING A BEHAVIOR OF THE DRIVER IN RESPONSE TO THE TRAFFIC EVENT

S1003 DETERMINING AN ATTENTION LEVEL OF THE DRIVER AT LEAST BASED ON A MATCH OF THE DETECTED BEHAVIOR OF THE DRIVER WITH AN EXPECTED BEHAVIOR IN RESPONSE TO THE TRAFFIC EVENT

DRIVER ATTENTION MONITORING

TECHNICAL FIELD

The present disclosure relates to driving safety enhancement, and more specifically, to a computer-implemented method, system and computer program product for monitoring driver attention.

BACKGROUND

Driving is a routine activity, and various improvements have been made to the road infrastructure and vehicle mechanical design to ensure driving safety. Nevertheless, driver inattention is still one of the primary causes of accidents and one of the challenging problems to be addressed for enhancing the driving safety.

For example, when performing a driving task, a driver may become distracted by something inside or outside the vehicle and thus lose focus on the road ahead, which can be very dangerous as it may lead to accidents due to lack of observation and slow response. Research shows that even a 2-second distraction may have a significant impact on the road safety. To ensure the driving safety, it is crucial to monitor and prevent driver distractions effectively.

SUMMARY

According to an embodiment of the present disclosure, there is provided a computer-implemented method for monitoring driver attention. In this method, a traffic event occurring during a driving task of a driver on a road can be monitored. A behavior of the driver in response to the traffic event can be detected. An attention level of the driver can be determined at least based on a match of the detected behavior of the driver with an expected behavior in response to the traffic event.

According to another embodiment of the present disclosure, there is provided a system for monitoring driver attention. The system comprises one or more processors, a memory coupled to at least one of the processors and a set of computer program instructions stored in the memory. When executed by at least one of the processors, the set of computer program instructions perform following actions. A traffic event occurring during a driving task of a driver on a road can be monitored. A behavior of the driver in response to the traffic event can be detected. An attention level of the driver can be determined at least based on a match of the detected behavior of the driver with an expected behavior in response to the traffic.

According to a yet another embodiment of the present disclosure, there is provided a computer program product for monitoring driver attention. The computer program product comprises a non-transitory computer readable storage medium having program instructions embodied therewith. The program instructions are executable by a processor to cause the processor to perform following actions. A traffic event occurring during a driving task of a driver on a road can be monitored. A behavior of the driver in response to the traffic event can be detected. An attention level of the driver can be determined at least based on a match of the detected behavior of the driver with an expected behavior in response to the traffic.

Accordingly, the attention level of the driver can be reliably predicted and the driver distraction can be efficiently prevented, thereby reducing the risk of a traffic accident and improving the driving safety.

BRIEF DESCRIPTION OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

DETAILED DESCRIPTION

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Figure 1:
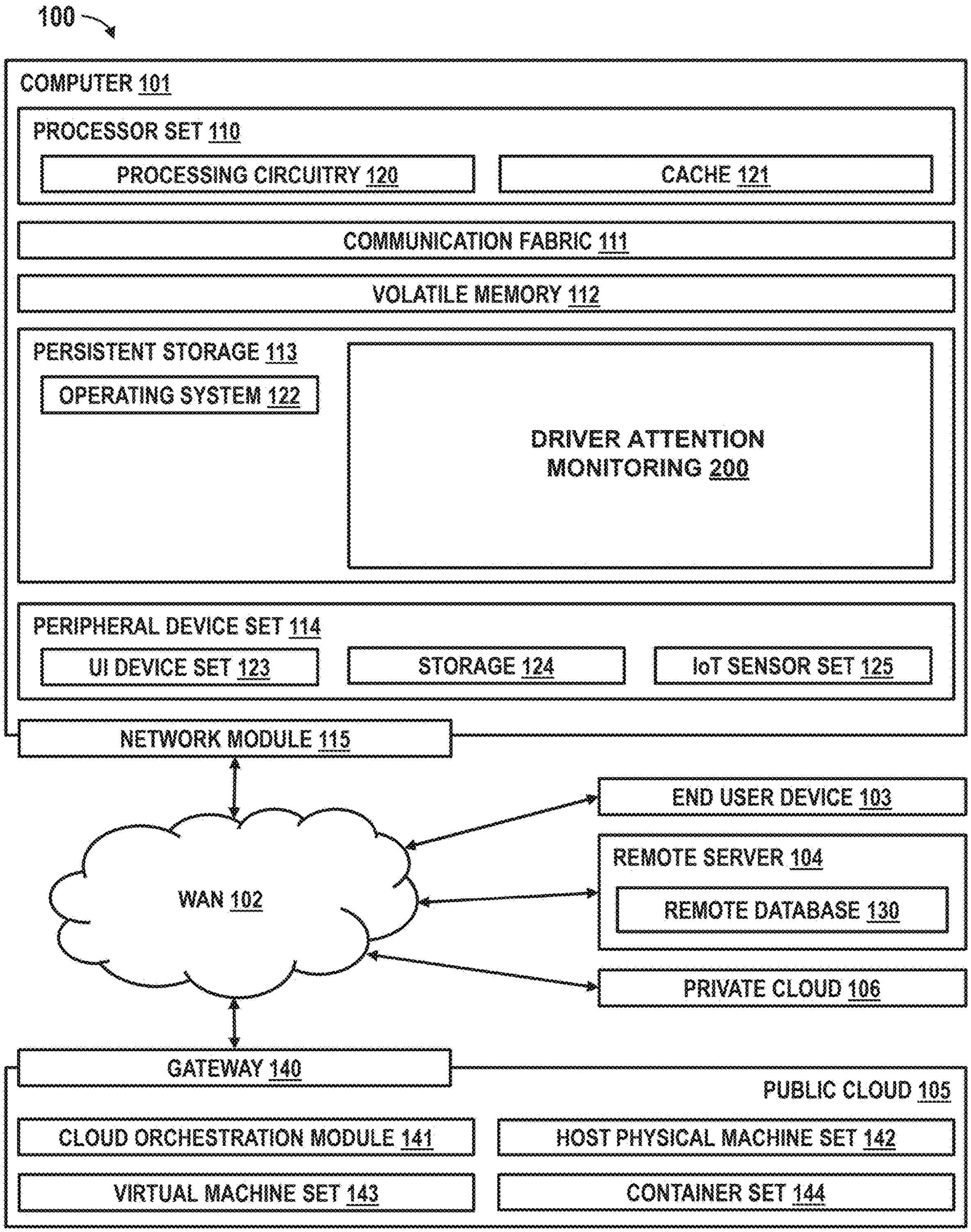
FIG. 1 shows an exemplary computing environment which is applicable to implement the embodiments of the present disclosure.

Referring to FIG. 1, computing environment 100 contains an example of an environment for the execution of at least some of the computer code involved in performing the inventive methods, such as driver attention monitoring 200. In addition to block 200, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and block 200, as identified above), peripheral device set 114 (including user interface (UI), device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

COMPUTER 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

PROCESSOR SET 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in block 200 in persistent storage 113.

COMMUNICATION FABRIC 111 is the signal conduction paths that allow the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

VOLATILE MEMORY 112 is any type of volatile memory now known or to be developed in the future. Examples include dynamic type random access memory (RAM) or static type RAM. Typically, the volatile memory is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

PERSISTENT STORAGE 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid state storage devices. Operating system 122 may take several forms, such as various known proprietary operating systems or open source Portable Operating System Interface type operating systems that employ a kernel. The code included in block 200 typically includes at least some of the computer code involved in performing the inventive methods.

PERIPHERAL DEVICE SET 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion type connections (for example, secure digital (SD) card), connections made though local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

NETWORK MODULE 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 103 is any computer system that is used and controlled by an end user (for example, a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

REMOTE SERVER 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

PUBLIC CLOUD 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

It is understood that the computing environment 100 in FIG. 1 is only provided for illustration purpose without suggesting any limitation to any embodiment of this disclosure, for example, at least part of the program code involved in performing the inventive methods could be loaded in cache 121, volatile memory 112 or stored in other storage (e.g., storage 124) of the computer 101, or at least part of the program code involved in performing the inventive methods could be stored in other local or/and remote computing environment and be loaded when need. For another example, the peripheral device 114 could also be implemented by an independent peripheral device connected to the computer 101 through interface. For a further example, the WAN may be replaced and/or supplemented by any other connection made to an external computer (for example, through the Internet using an Internet Service Provider).

As mentioned above, driver inattention has been one of the challenging problems to be addressed for enhancing the driving safety. There are existing approaches to detect certain types of driver inattention, such as fatigue or distraction by road objects or in-car activities. The existing approaches may enable the detection of driver inattention by monitoring the driver's eye and head movements. For example, driver inattention can be detected if the driver's eyes are not on the road ahead but on his or her mobile phone, or if the driver's eyes are closed too often or for too long due to drowsiness. However, the existing approaches cannot cope with driver distractions caused by mind wandering or mind thinking, because when the mind-thinking distraction occurs, the drivers may not appear sleepy, their eyes remain fixed ahead, and they appear to be controlling the car as usual. Therefore, the existing approaches cannot provide a reliable driver attention evaluation.

In view of the above, there exists a need for an improved driver attention monitoring approach to efficiently monitor driver attention and prevent driver distraction, thereby enhancing the driving safety.

Embodiments of the present disclosure aim to solve at least one of the technical problems described above, and propose a method, a system and computer program product for monitoring driver attention. In the driver attention monitoring approach according to embodiments of the present disclosure, a driver's behavior in response to a traffic event, such as detected movements of other road objects, detected changes of traffic lights, can be monitored. Then, the driver's behavior can be matched against an expected behavior, such as a reasonable behavior that most experienced drivers will take in response to the traffic event. Accordingly, the attention level of the driver can be evaluated based on how closely the driver's behavior matches with the expected behavior.

For example, the traffic event may be one of the traffic events commonly occurring inside or outside the vehicle and requiring the driver's adequate attention and prompt responsive action, and it can be correlated with an expected behavior in advance based on statistical data regarding driving activities. In such a way, the attention level of the driver can be evaluated based on a match of the detected behavior with the expected behavior, to efficiently and reliably identify various types of driver distractions and to determine whether the driver's attention is still on the driving activity, even for the mind-wandering distraction as mentioned above.

On the other hand, an interactive chat closely related to a potential driver distraction, such as an improper behavior of the driver in response to the traffic event, can be initiated if needed, to draw the driver's attention back to the driving task. Additionally, the interactive chat can be used to further evaluate the driver's attention level, for example, based on the answers provided by the driver during the chat.

Accordingly, the attention level of the driver can be reliably predicted, and the driver distraction can be efficiently prevented, thereby reducing the risk of a traffic accident, and improving the driving safety.

Figure 2:
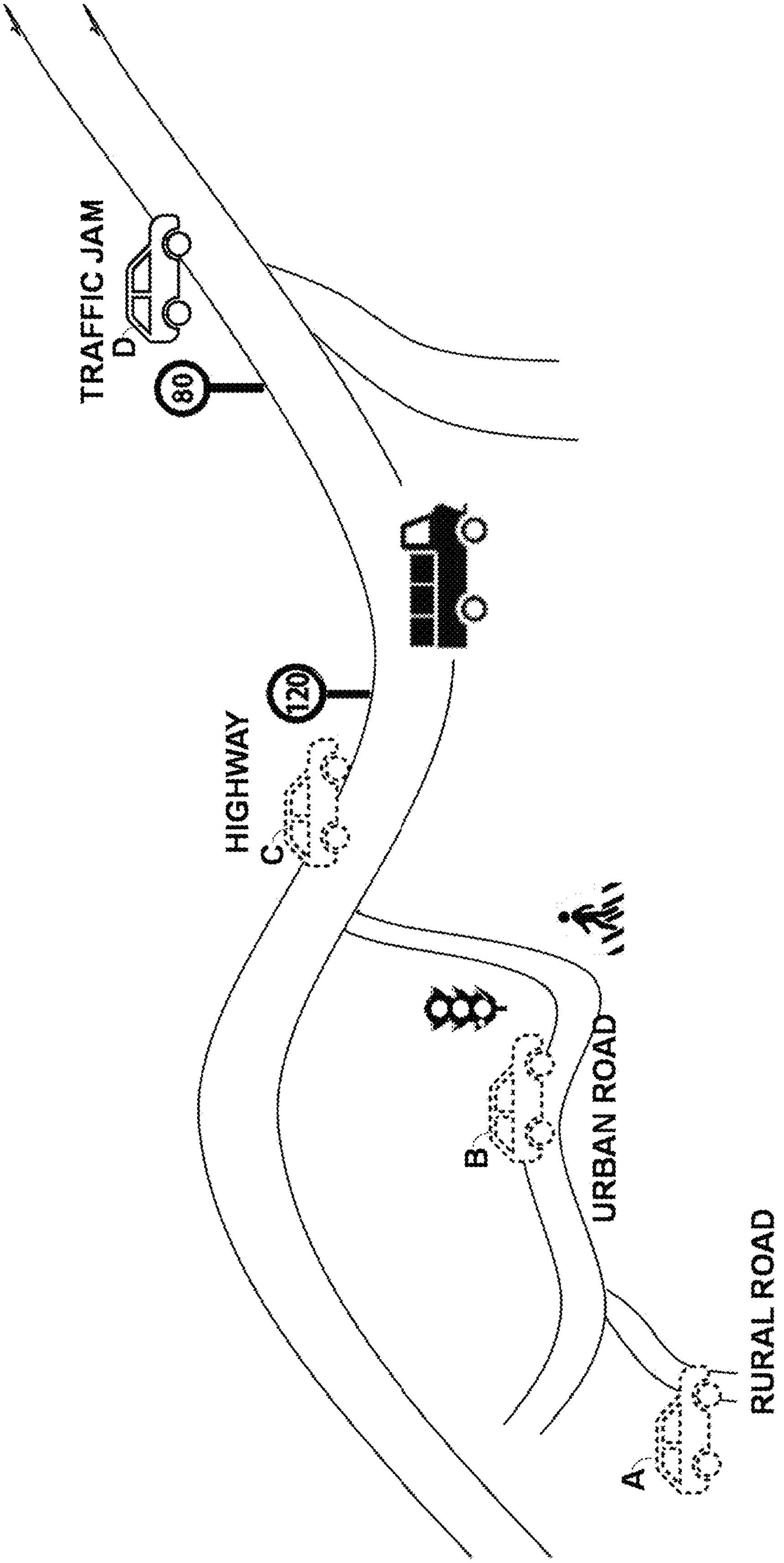
FIG. 2 shows an exemplary scenario for driver attention monitoring according to an embodiment of the present disclosure.

FIG. 2 shows an exemplary scenario for monitoring driver attention according to an embodiment of the present disclosure.

As shown in FIG. 2, a driver may drive his or her car (hereinafter referred to as a host vehicle) and pass a series of locations A, B, C and D during a driving task on the road. During the trip, the driver needs to focus on and pay attention to a variety of road objects and various changes in the driving environment of the car, such that appropriate decisions can be made in view of the driving environment to safely reach an intended destination. For example, the road objects in the driving environment may include but not limited to obstacles, pedestrians, other nearby vehicles, traffic signals and signs, and the changes in the driving environment may include but not limited to changes in the type, geometry and traffic density of the roadway in which the host vehicle travels.

For example, the driver first can drive the car on a rural road at location A, on an urban road at location B later, then enters a highway at location C, and finally encounters a traffic jam at location D while driving on the highway. Along the way from the location A to location D, there may be many traffic events occurring during the driving task, for example, a truck overtakes the host vehicle, a pedestrian runs into the lane in which the host vehicle travels, an alert or navigational guidance is issued from a navigational system of the host vehicle or a navigation application of the driver's mobile phone. The traffic events may require the driver's adequate attention and corresponding prompt responsive actions. Accordingly, the driver's responsive behavior in response to the detected traffic event(s) can be monitored to determine whether the driver's attention is still on the driving task. It should be noted that the above road objects and traffic events described in combination with FIG. 2 are just examples, the present disclosure are not limited thereto.

Figure 3:
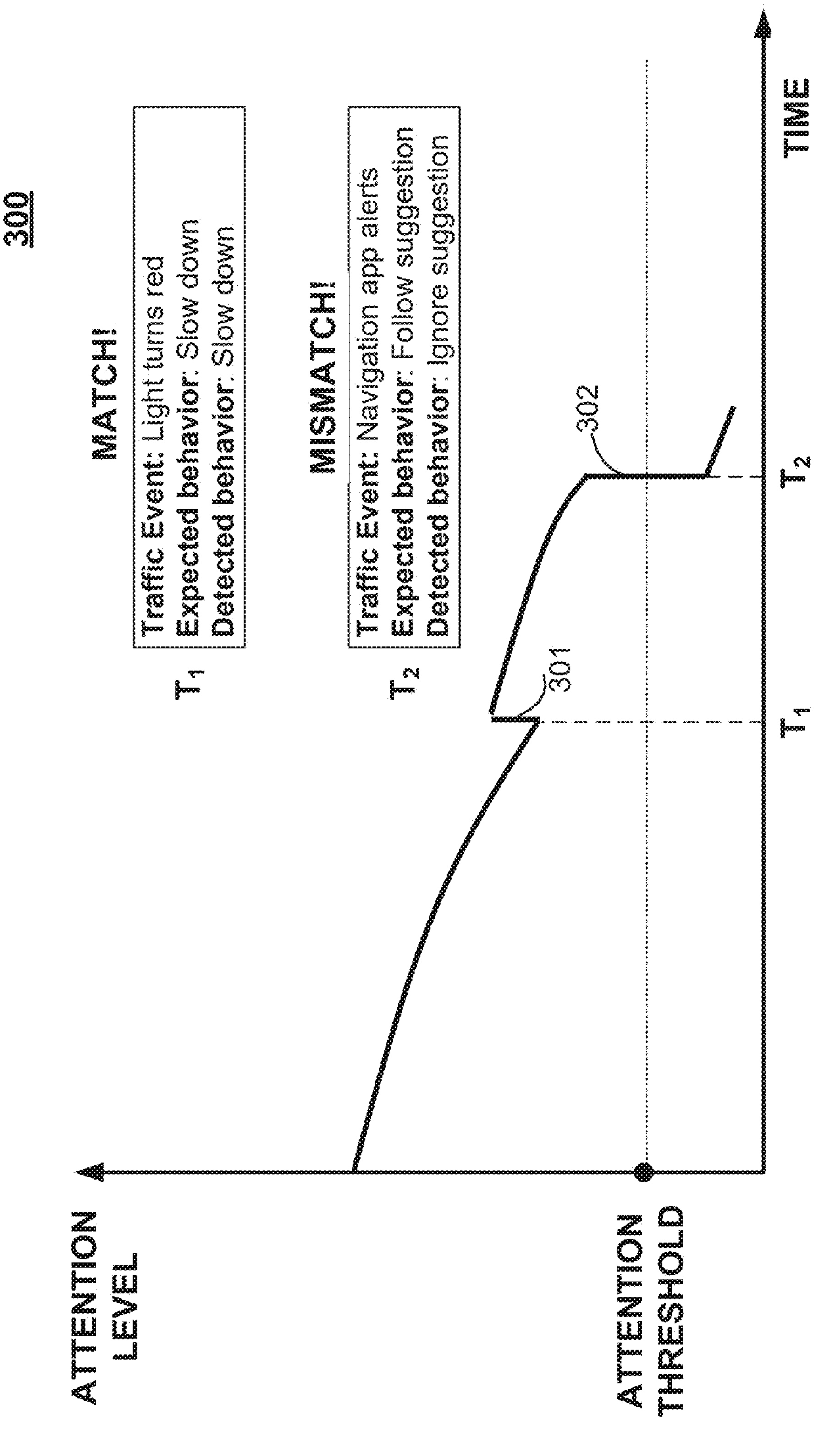
FIG. 3 shows an exemplary schematic diagram of driver attention monitoring based on a detected driver behavior in response to a traffic event according to an embodiment of the present disclosure.

FIG. 3 shows an exemplary schematic diagram of driver attention monitoring based on a detected driver behavior in response to a traffic event according to an embodiment of the present disclosure.

As shown in FIG. 3, the attention level of the driver may generally conform to a degradation curve 300 with respect to time, which means that in the ideal case, the attention level may smoothly degrade at a certain gradient over time during the driving task. The curve may be further impacted by a match or mismatch of the detected behavior with the expected behavior in response to a monitored traffic event, as can be seen at the upward and downward fluctuations of the curve. As examples of the fluctuations of the curve, at the point of time $T_1$, an attention increasing event of the driver can be identified based on a match of the detected behavior with respect to the expected behavior, which results in an upward fluctuation of the curve, while at the point of time $T_2$, an attention decreasing event of the driver can be identified based on a mismatch of the detected behavior with respect to the expected behavior, which results in a downward fluctuation of the curve.

For example, at the point of time $T_1$, a traffic event of a traffic light turning red can be monitored, and the expected behavior in response to this traffic event should be slowing down, such that the vehicle can be safely stopped to avoid collision. In this example, the observed behavior of the driver is also slowing down, which matches the expected behavior and indicates that the driver is in an attentive state. Therefore, the attention level is increased by a reward value at the point of time $T_1$, as indicated by reference number 301.

At the point of time $T_2$, a traffic event of navigation application alerting, which, for example, alerts the driver to slow down or alerts the driver that the host vehicle has gone out of the main road, can be monitored. The expected behavior in response to this traffic event should be following the navigational suggestion from the application, such that the vehicle can be safely manipulated. In this example, the observed behavior is ignoring the navigational suggestion, which does not match the expected behavior and indicates that the driver is in an inattentive state. Therefore, the attention level is decreased by a punishment value at the point of time $T_2$, as indicated by reference number 302.

In some cases, in addition to the match of the detected behavior with the expected behavior, the determining of the attention level of the driver can be further based on an explanation to the detected behavior provided by the driver. For example, the driver may be in a hurry and thus travelling at high speed for a trip, and the driver was alerted due to the over-speed event. In response to the alert, the driver gave a reasonable explanation why he or she needs to go fast, and the reasonable explanation can also be used in the evaluation of whether the driver's behavior is appropriate. In this case, even if there is a mismatch of the detected behavior with the expected behavior for the overspeed event during the trip, the detected behavior of the driver may be deemed reasonable and not regarded as a driver distraction, and thus the attention level does not to be decreased by a punishment value.

It should be noted that although FIG. 3 only illustrates two traffic events detected in the environment of host vehicle, various traffic events can be detected and used for evaluating the driver's attention level based on a match of an observed behavior with the expected behavior for such traffic events. As an example, the traffic event may include a vehicle assistance system altering the driver, for example when the host vehicle deviates from the current lane of travel or when the host vehicle follows too close to its front car, and the expected behavior should be a timely correction manipulation by the driver. As another example, the traffic event may include another car merging into the lane in which the host vehicle travels, and the expected behavior should be the driver timely honking at the car or slowing down the host vehicle. As a further example, the traffic event may include the host vehicle changing the lane of travel or turns at an intersection, and the expected behavior should be the driver's eyes checking the side-view mirror. In these examples and additional examples not listed in the present disclosure, the observed behavior of the driver is matched against the expected behavior, and the attention level of the driver can be determined based on a match result of the behaviors, such as a match or mismatch, or a matching degree for the behaviors).

It should be noted that the attention level of the driver can be determined in different ways based on the match result. For example, an absolute value of the attention level or a relative adjustment to the current attention level can be determined based on the match result. It should be noted that the present disclosure does not restrict the detailed way of determining the attention level based on the match result.

In some embodiments, an incremental value (e.g., the reward value as mentioned above) or a decremental value (e.g., the punishment value as mentioned above) can be determined based on a match or mismatch or match degree of the detected behavior with the expected behavior, and then applied to the current attention level of the driver, as described in the embodiments of FIG. 3.

In other embodiments, an absolute value of the attention level can be determined based on the match result. In an illustrative example, the absolute value of the attention level can be determined proportionally to the match degree between the detected behavior and the expected behavior. For example, a higher score of the attention level can be determined if the driver's behavior closely matches the expected behavior, while a lower score of the attention level can be determined if the driver's behavior does not match well with the expected behavior.

Further as shown in FIG. 3, at the point time of $T_2$, the attention level of the driver falls below an attention threshold, which means that the driver may lose attention to the driving task and there may be a high risk of traffic accidents. In response to the determined attention level of the driver falling below an attention threshold, an interactive chat can be initiated, if needed, to draw the driver's attention back to the driving task. Additionally or alternatively, the interactive chat can be initiated on a periodic basis as a precautionary measure, such that the driver can be regularly reminded to focus on the driving task. The interactive chat can also be used to further evaluate the driver's attention level based on the driver's answers during the chat, which will be described in combination with FIG. 4 hereinafter.

Figure 4:
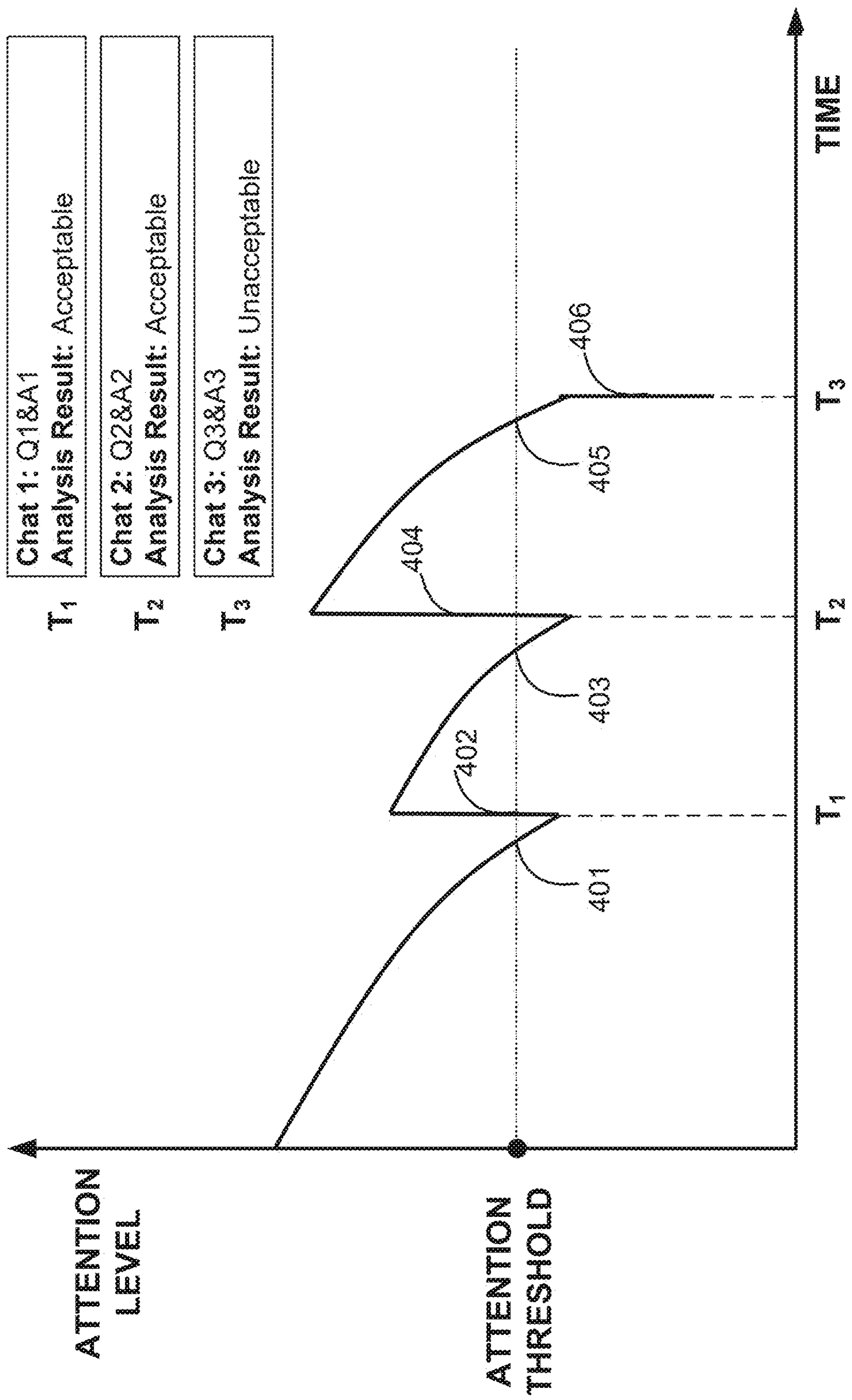
FIG. 4 shows an exemplary schematic diagram of driver attention monitoring based on an answer acquired from the driver during an interactive chat according to an embodiment of the present disclosure.

FIG. 4 shows an exemplary schematic diagram of driver attention monitoring based on an answer acquired from the driver during an interactive chat according to an embodiment of the present disclosure.

As shown in FIG. 4 and similar to the degradation curve 300 of FIG. 3, the attention level of the driver may also conform to a degradation curve 400 with respect to time, which curve may be further impacted by a result of whether the answer is acceptable with respect to the question asked during the interactive chat. According to embodiments of the present disclosure, the answer with respect to the question of the interactive chat can be acquired from the driver. Then, the attention level of the driver can be determined based on whether the acquired answer is acceptable, for example, by evaluating a response time and/or response content of the answer.

As indicated by reference number 401, it can be detected that the attention level of the driver falls below the attention threshold, for example, based on the match result of the driver's behavior with the expected behavior. At this time, an interactive chat "Chat 1" can be initiated by asking the driver a question "Q1" related to the context of the driving task and acquiring an answer "A1" from the driver. At the point of time $T_1$, based on evaluating the response time and/or response content of the answer, it can be determined whether the answer of the driver is acceptable.

For example, when the driving environment is not busy but the driver's answer is provided after some time rather than immediately, it may indicate that the driver might have lost attention but now the driver's attention is back to the driving task, so the driver's answer can be determined as an acceptable answer and the attention level should be increased by a value accordingly. As another example, when the answer indicates that the driver could not hear clearly and thus asks to repeat the question, or when the answer indicates that the driver does not know the answer and thus asks for the answer, it may similarly indicate that the driver might have lost attention but the driver's attention is back to the driving task. In such cases, an attention increasing event of the driver can be identified based on the reasonability of the answer, and the attention level of the driver can be increased by a reward value at the point of time $T_1$, as indicated by reference number 402.

As indicated by reference number 403, it can be detected that the attention level falls below the attention threshold again. At this time, an interactive chat "Chat 2" can be initiated by asking the driver a question "Q2" and acquiring an answer "A2" from the driver. At the point of time $T_2$, it can be determined that the answer of the driver is also acceptable, and thus the attention level can also be increased by a reward value at the point of time $T_2$, as indicated by reference number 404.

For example, if a timely answer is provided within 1 second, and the answer well matches an expected response or qualifies as a reasonable explanation, it may indicate that the driver keeps his or her full attention on the driving activity, and thus it can be determined that the driver's answer is acceptable.

It should be noted that the reward value at the point of time $T_2$ is larger than that of the point of time $T_1$ since the answer provided by the driver for Chat 2 indicates that the driver is more focused on the driving task at the point of time $T_2$.

As indicated by reference number 405, it can be detected that the attention level falls below the attention threshold again. At this time, an interactive chat "Chat 3" can be initiated by asking the driver a question "Q3" and acquiring an answer "A3" from the driver. At the point of time $T_3$, it can be determined that the driver's answer is unacceptable, and the attention level can be decreased by a punishment value at the point of time $T_3$, as indicated by reference number 406. For example, if the driver provides no answer or provides a meaningless answer, it may indicate that the driver has lost attention on the driving activity. In this case, an attention decreasing event of the driver can be identified based on the acquired answer, and the attention level can be decreased by the punishment value, as mentioned above.

According to embodiments of the present disclosure, there may be various criteria for determining whether the driver's answer is acceptable, for example, based on whether the response time of the answer satisfies a promptness requirement and/or whether the response content of the answer qualifies as an acceptable answer.

It should be noted that the criteria for determining whether the driver's answer is acceptable described in combination with FIG. 4 are only examples of the present disclosure, it can be contemplated that the analysis of the reasonability of the answers can be implemented in other ways. In addition, the attention level of the driver determined based on a delta value (i.e., the reward or punishment value) applied to the current attention level in the embodiment of FIG. 4 is only an illustrated example, it can be contemplated that in other embodiments, an absolute value of the attention level can also be determined based on the evaluating of the response time and/or response content of the answer.

For example, the absolute value of the attention level of the driver can be determined based on an acceptable or reasonable degree of the driver's answer. For example, a higher score of the attention level can be determined if the driver's answer is more reasonable, while a lower score of the attention level can be determined if the driver's answer is less reasonable. It should be noted that the acceptable or reasonable degree of the driver's answer can be determined based on various types of semantic analysis on the acquired answer, details are omitted here.

According to embodiments of the present disclosure, the generation of question and the evaluation of answer can be implemented in various manners for the interactive chat. The basic rules for the generating the question is that answering the question does not need much thinking by the driver and should not impact the driver's normal driving of the host vehicle. Therefore, the question should be highly dependent on the context of the driving task, otherwise, an irrelevant question would further occupy the driver's attention unnecessarily. It should be noted that the context of the driving task may involve various factors related to the current environment of the driving task and the driver's operations during the driving task, which may indicate a current situation or state of the driving task. For example, the factors may include but not limited to: various road objects detected in the environment of the host vehicle, such as pedestrians, roadside objects, and other vehicles, which may be potential collision objects; a condition of the roadway in which the driver travels, such as the speed limit, road type, lane assignment and traffic density of the road; a behavior of the driver which may lead to a potential accident, for example, the driver exceeds the speed limit. In this way, the question asked to the driver is closely related to potential hazards associated with the driver's improper behavior, thereby drawing the driver's attention back as soon as possible.

As an example, the question of the interactive chat can be selected from a plurality of questions in a question & answer (Q&A) library, and the driver's answer can be evaluated based on a match with the expected answer(s) in the Q&A library.

As another example, both the generation of the question and evaluation of the answer for the interactive chat can be implemented with the aid of a language model, such as a Natural Language Processing (NLP) model or a large language model (LLM), which will be described in FIG. 5 hereinafter.

Figure 5:
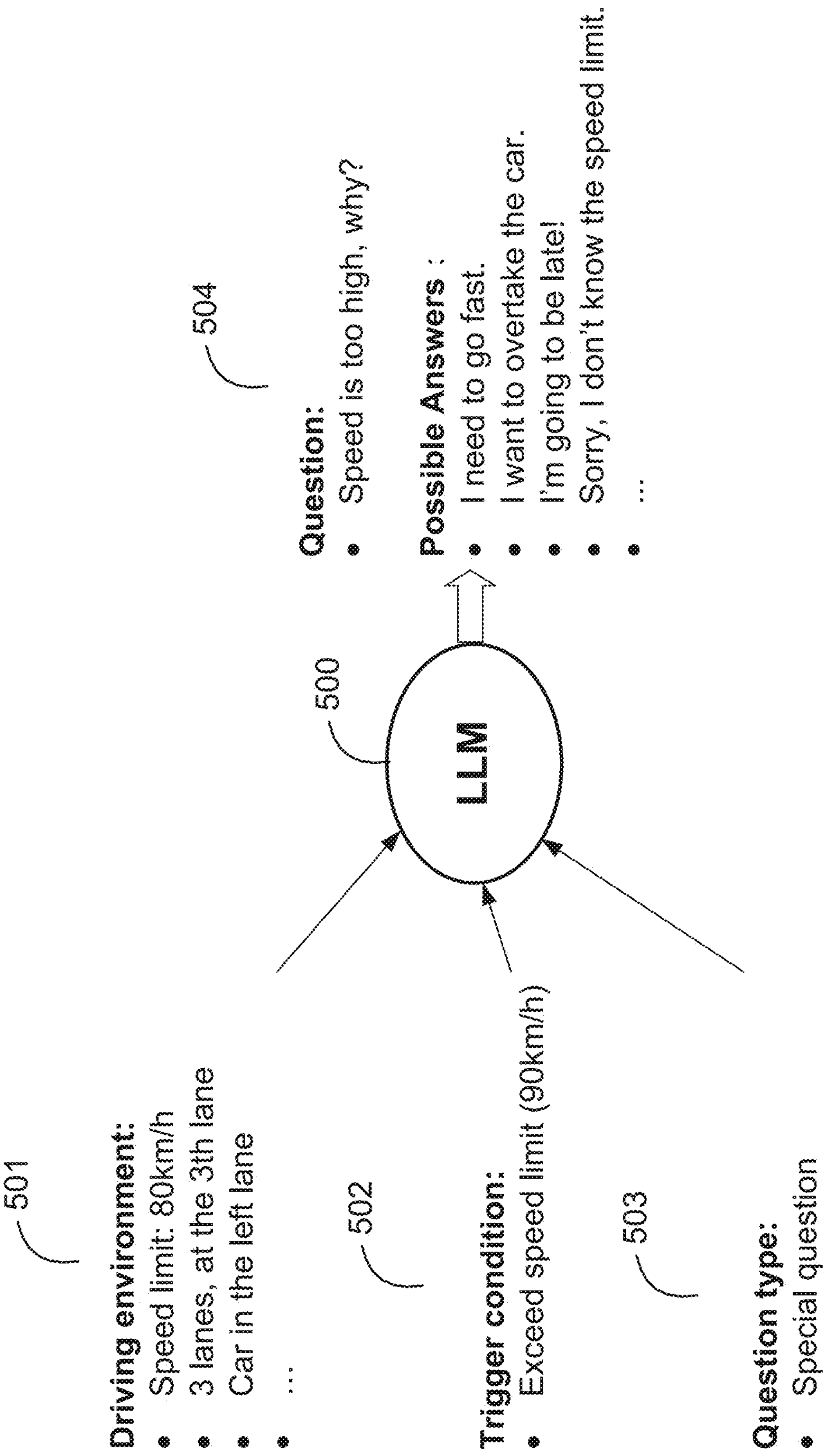
FIG. 5 shows an exemplary schematic diagram of a language model for generating an interactive chat according to an embodiment of the present disclosure.

FIG. 5 shows an exemplary schematic diagram of a language model for generating an interactive chat according to an embodiment of the present disclosure.

As shown in FIG. 5, the language model may be implemented as a large language model (LLM) 500 in a chat generation task, and can be used to generate the question for the interactive chat based on the context of the driving task, and to evaluate the acceptability of the answer acquired from the driver. According to embodiments of the present disclosure, LLM 500 can take the driving environment 501, the trigger condition 502, and optionally the question type 503 as inputs, and provide a question to be asked to the driver and one or more expected answers associated therewith, as indicated by reference number 504. In this example, driving environment 501 and trigger condition 502 are input to LLM 500 as the context of the driving task, which indicates the current situation of the driving task. Details for the structure of the LLM is known to those skilled in the art, and thus omitted herein.

For example, driving environment 501 may involve the speed limit for the lane of travel, the geometry for the lanes of the roadway, the lane assignment for the host vehicle, and other information describing the environment in which the host vehicle drives. Trigger condition 502 may involve an identified driver distraction, for example, the driver exceeding the speed limit due to distraction, which may be identified based on a mismatch with the expected behavior.

Optionally, question type 503 can be used in the selection of a proper question type among different question types. As an example, the selection of the question types can be based on the context of the driving task. In this example, a simple alert and echo question type is selected for a busy driving environment, so that the driver just needs a simple echo and is not disturbed seriously; a general question type is selected for a normal driving environment, which requires the driver to answer yes or no; and a special or open question type can be selected for a relaxed driving environment. As another example, the selection of the question types can be based on the preference of the driver. In this example, a simple or general question type can be selected for new drivers since they tend to be disturbed by the questions, and a special question type can be selected for drivers who like chatting during the trip.

In the illustrated example of FIG. 5, when the driver distraction is related to an over-speed event which may be caused by mind wandering, the question asked to the driver may be "Speed is too high, why?", and the expected answers to the question may be "I need to go fast.", "I want to overtake the car.", "I'm going to be late!", "Sorry, I don't know the speed limit.", and the like. Accordingly, the attention level of the driver can be updated based on a match of the response content of the driver's answer with the expected answer(s) generated with the aid of the LLM. If there is a match, the attention level of the driver can be increased by a reward value, otherwise, the attention level of the driver will be decreased by a punishment value.

Figure 6:
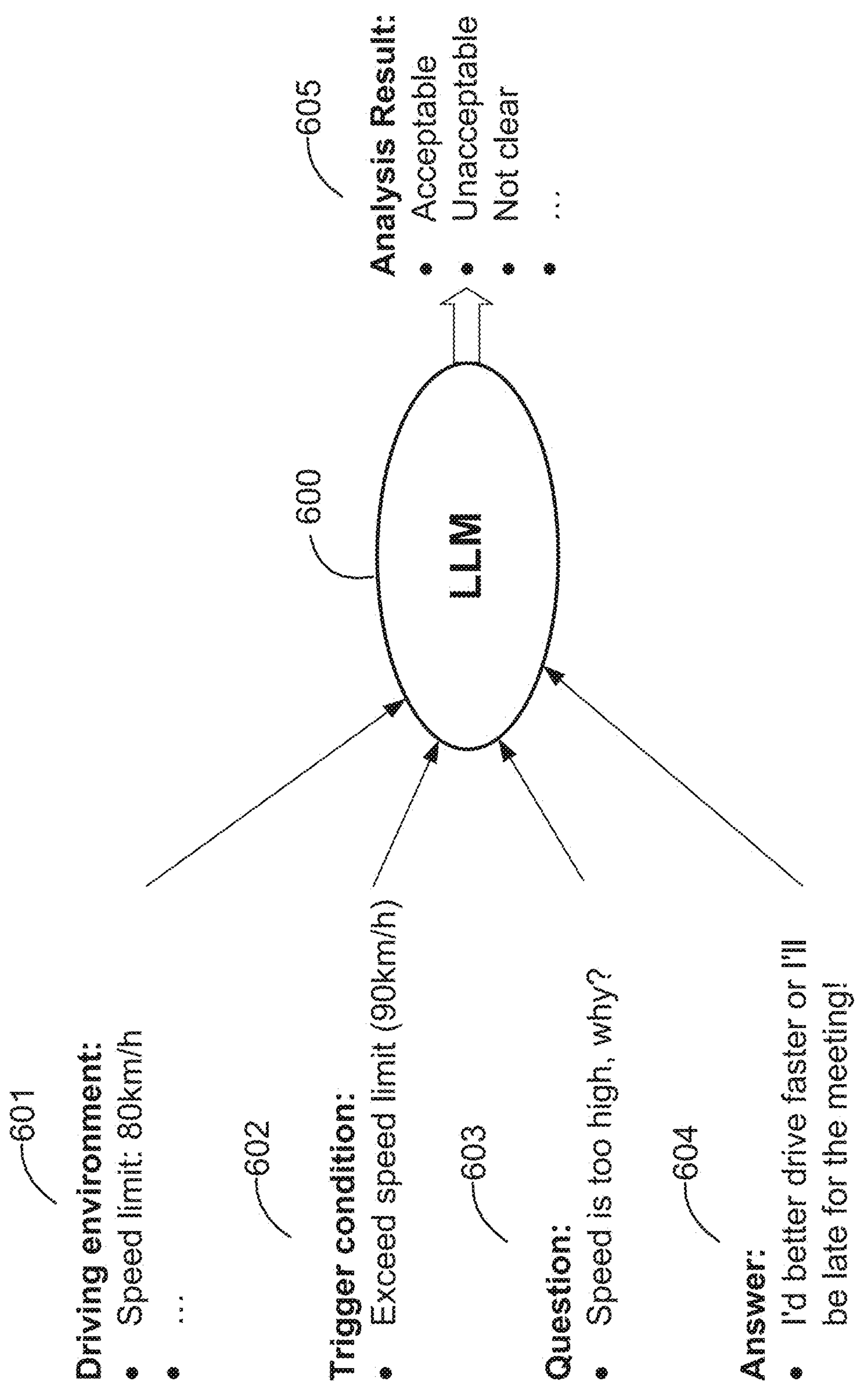
FIG. 6 shows an exemplary schematic diagram of a language model for evaluating the driver's answer acquired during the interactive chat according to an embodiment of the present disclosure.

FIG. 6 shows an exemplary schematic diagram of a language model for evaluating the driver's answer acquired during the interactive chat according to an embodiment of the present disclosure.

As shown in FIG. 6, the language model is implemented as LLM 600, and a driving environment 601, a trigger condition 602, a question asked to the driver 603, and an answer acquired from the driver 604 can be input to LLM 600, in order to evaluate whether the driver's answer is reasonable or acceptable, such that LLM 600 can provide an analysis result 605 to confirm whether the driver is in an attentive state or in an inattentive state. It should be noted that driving environment 601, trigger condition 602 and question 603 can be the same as those depicted in FIG. 5, and LLM 600 can be a same or different language model with respect to LLM 500 of FIG. 5.

In the embodiment of FIG. 6, a semantic analysis of the response content of answer 604 can be conducted in combination with the context of the driving task (involving driving environment 601, and trigger condition 602) and the previously generated question 603 with the aid of LLM 600, such that the attention level of the driver can be updated based on the analysis result 605. For example, when the analysis result indicates that the answer is acceptable, the attention level of the driver can be increased by a reward value, and when the answer is unacceptable or not clear, the attention level can be decreased by a punishment value.

It should be noted that the above questions and possible answers are only examples but not restrictions to the present disclosure. Other questions can also be generated to alert and test the driver, for example, the question "The light is red, I don't think you can get through the junction in 3 minutes." can be generated when the traffic light turns red in 20 meters but the driver does not slow down; the question "Is there a car on your right?" can be generated when the driver turns right but does not check the right mirror; the question "Are you following that car?" can be generated when the driver follows the car for a long time; the question "Do you want to change lanes?" can be generated when the driver deviates from the current lane of travel.

According to the embodiments of FIG. 5 and FIG. 6, the generative chat can be used to alert and test the driver to ensure that the driver still focuses on the driving activity, and the interactive voice chat can be provided as an experienced friend in the passenger seat, thereby enhancing the driving safety. In addition, since the question of the interactive chat is generated closely related to the context of the driving task, the driver can be immediately aware of the related hazard in the driving environment and the contributing factor for initiating the interactive chat, so that the driver can restore the attention level to an acceptable level and then take proper driving actions as soon as possible.

Figure 7:
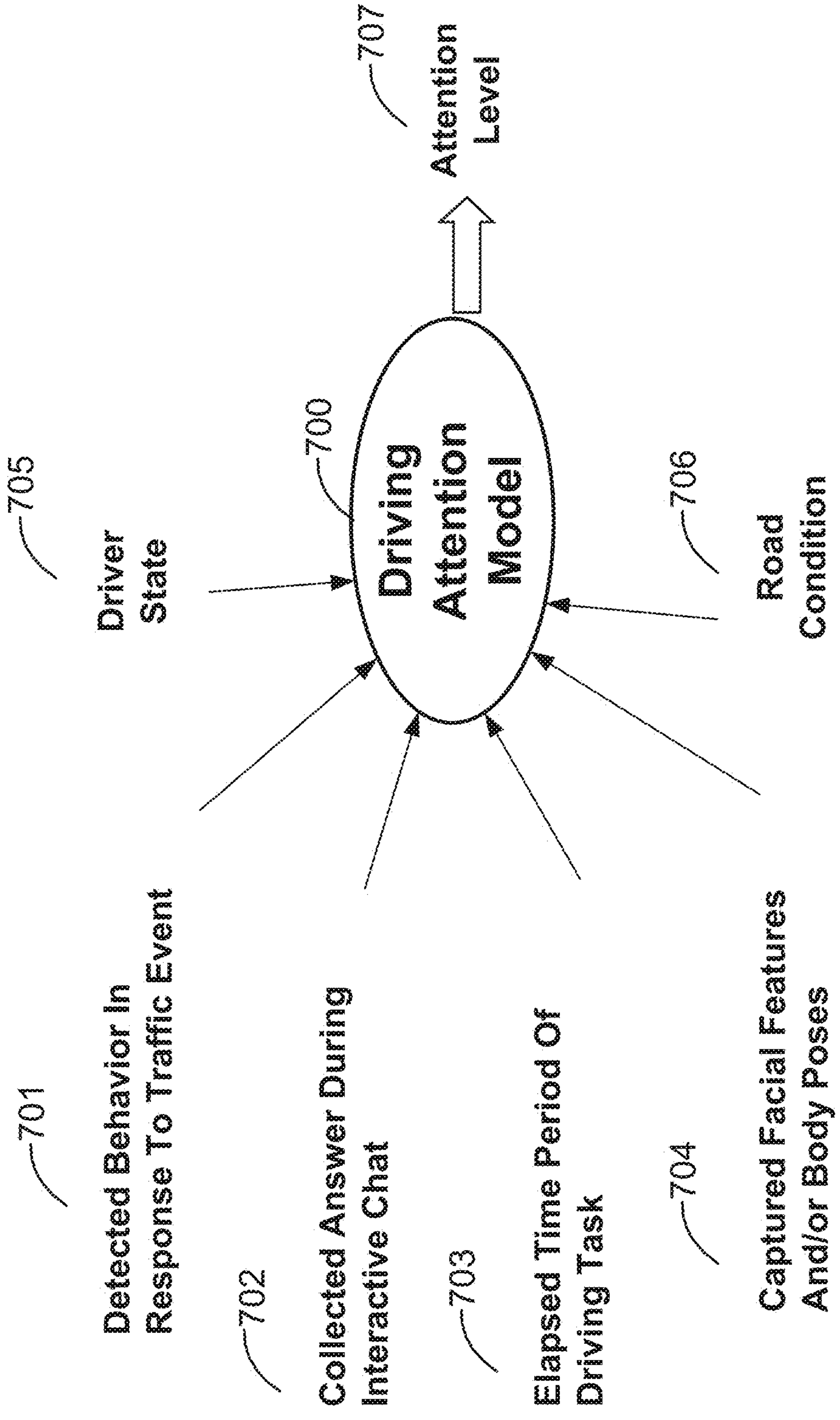
FIG. 7 shows an exemplary schematic diagram of a driving attention model for determining an attention level of the driver according to an embodiment of the present disclosure.

FIG. 7 shows an exemplary schematic diagram of a driving attention model for determining an attention level of the driver according to an embodiment of the present disclosure.

As shown in FIG. 7, various factors can be considered in the driving attention model 700 to comprehensively determine the attention level 707 of the driver. In particular, the attention level can be impacted by various factors such as an elapsed time period of the trip, the driver states, and road conditions. For example, even experienced drivers may be distracted during long drives, older drivers may have more trouble paying attention to the road than younger drivers, it is easier to get distracted on highways, road with fewer cars, and familiar roads, and the like.

Accordingly, the factors considered in the determination of the attention level can include one or more of the detected behaviors of the driver in response to the traffic event 701 (as described in combination with FIG. 3), the acquired answer of the driver during the interactive chat 702 (as described in combination with FIG. 4), the elapsed time period of the driving task 703, the captured facial features and/or body pose of the driver during the driving task 704, the driver state(s) 705, and the road condition(s) 706, among other examples.

The detailed descriptions about the contribution of the detected behavior 701, the acquired answer 702 and the elapsed time period 703 to the determination of the attention level 707 can refer to the content described with respect to FIG. 3 and FIG. 4. Hereinafter, the contribution of the captured facial features and/or body poses 704, the driver state 705 and the road condition 706 will be described.

In a first example, the facial features and/or body poses 704 considered in the determination of the attention level 707 by the driving attention model 700 comprises one or more of detected open lips, quick blinking, finger tapping, and the like. It should be noted that since different drivers may present different, personalized facial features and/or body poses when they lose attention during the driving tasks, the captured facial features and/or body poses can be customized to a particular driver, rather than common features such as eye/head movement that can be found in every driver when he or she loses attention.

Specifically, the driver's face and body state can be acquired using various computer vision techniques, and the driver's attention level can also be continuously monitored to identify any driver distraction, such as an unmatched behavior in response to a traffic event, an unacceptable answer during the interactive chat, and the like. Accordingly, those facial features and/or body poses (such as detected open lips, quick blinking, finger tapping, and the like) of that driver found to be closely related to the driver's distraction can be correlated with the occurrence of the driver's distraction, and the facial features and/or body poses can be labeled with a distraction flag specific to that driver. In this way, for future drives, as long as any of the above-mentioned facial features and/or body poses can be observed, the attention level of that driver can be adjusted by applying a punishment value thereto, since the facial features and/or body poses can be a forecast of that driver's distraction.

In a second example, the driver state 705 considered in the determination of the attention level 707 by the driving attention model 700 comprises one or more of an age, a gender, a driving experience, an emotional state of the driver, and the like.

In a third example, the road condition 706 considered in the determination of the attention level 707 by the driving attention model 700 comprises one or more of a type, a geometry, a traffic density of the road, and the like. For example, highways and main roads have steep gradients, such as the gradient for the degradation curve, while country roads have gentle gradients; familiar roads with few cars have steep gradients, while crowded roads have gentle gradients; and the like.

According to embodiments of the present disclosure, the driving attention model can be implemented as a parametric model, such that the attention level can be determined, as long as the information regarding the driving context, the driver, the road (e.g., as indicated by reference number 701 through 706) is available and provided as inputs to the model. It should be noted that the factors indicated by reference number 701 through 706 are only examples of the factors considered in the determination of the attention level, other additional factors can also be contemplated to comprehensively evaluate the attention level of the driver.

Figure 8:
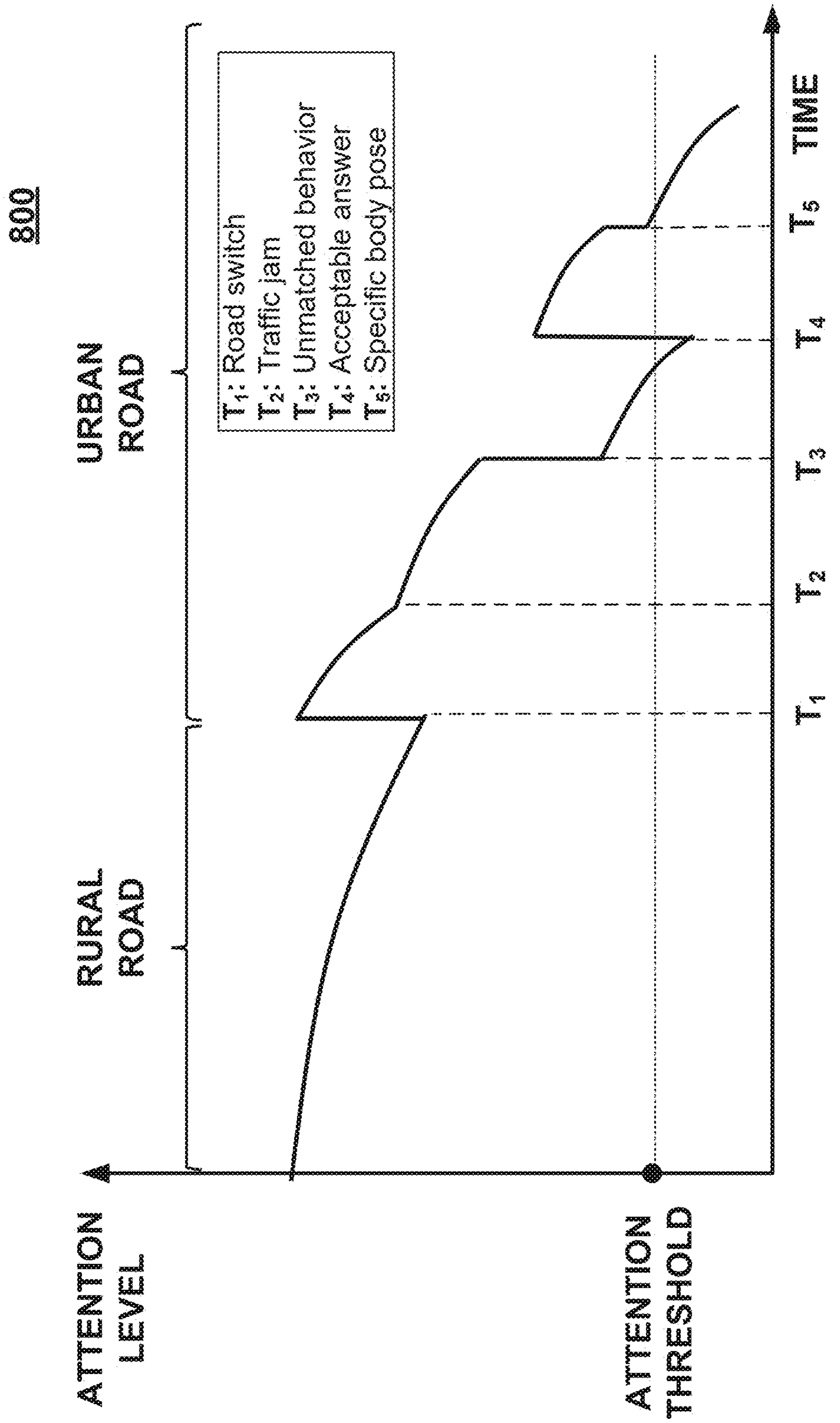
FIG. 8 shows an exemplary schematic diagram of driver attention monitoring based on various factors detected during a driving task of the driver according to an embodiment of the present disclosure.

FIG. 8 shows an exemplary schematic diagram of driver attention monitoring based on various factors detected during a driving task of the driver according to an embodiment of the present disclosure.

As shown in FIG. 8 and similar to the degradation curve 300 of FIG. 3 and the degradation curve 400 of FIG. 4, the attention level of the driver may generally conform to a degradation curve 800 with respect to time, which curve may be further impacted various factors detected during the driving task. For example, as described in combination with FIG. 7, the factors considered in the determination of the attention level of the driver include one or more of: the detected behavior of the driver in response to the traffic event, the acquired answer of the driver during the interactive chat, the elapsed time period of the driving task, the captured facial features and/or body pose of the driver during the driving task, the driver state and the road condition, among other examples.

For example, at the point of time $T_1$, there is a change in the road type from rural road to urban road during the driving task, and the attention level is increased by a value due to the road type change. At the point of time $T_2$, there is a traffic jam on the road during the driving task, and the gradient for the degradation curve is reduced. At the point of time $T_3$, a traffic event is detected, but the driver's behavior in response to the detected traffic event does not match the expected behavior, so the attention level is decreased by a punishment value. Later, at some time before the point of time $T_4$, the attention level falls below the attention threshold, so an interactive chat is initiated to alert and test the driver's attention, and the driver's answer during the chat is also acquired. At the point of time $T_4$, the driver's answer is determined as an acceptable answer, for example, based on the response time and/or response content, and the attention level is increased by a reward value. At the point of time $T_5$, the driver's specific body pose, such as finger tapping which was found to be highly related to that driver's distraction, can be captured, and the attention level is decreased by a punishment value.

According to embodiments of the present disclosure, a multi-channel attention promotion can be provided to increase the level of attention until the attention score of the driver is above a safe level. For example, it can be determined whether the attention level of the driver falls below the attention threshold, and as a response, control signals can be provided to one or more vehicle components for attention promotion, until the attention score of the driver is above the safe level.

As an example, if the attention state of the driver is from distraction to attention and the attention level of the driver is not too low, the navigator on the vehicle platform may be controlled to provide visual and/or audio alerts, e.g., "someone may come out from behind the stopped car!", such that the driver can be informed of the risks on the road. As another example, the entertainment system of the vehicle platform may be controlled to play music to the driver, such that the secondary attention of the driver is not empty, which may reduce the risk of the distraction caused by the driver's mind wandering, otherwise, the driver may think about other things and lose attention. As an additional example, the navigation application can be controlled to define a navigational task, such as checking the right mirror, and monitor the performance of the task by the driver. As another example, the navigation application of the mobile phone and/or the navigator on the vehicle platform can also be controlled to suggest the driver to stop and have a rest when the attention level is too low. Additionally or alternatively, the attention promotion mechanism can include an integrate control of the in-car systems, such as windows, seat temperature control, hazard lights, driving assistance, so that the driver will not be apportioning his or her attention on less important matters.

Other proper attention promotion mechanisms can also be contemplated to improve the driver's attention until the safe level can be reached. The present disclosure does not restrict the types of the promotion mechanisms.

Figure 9:
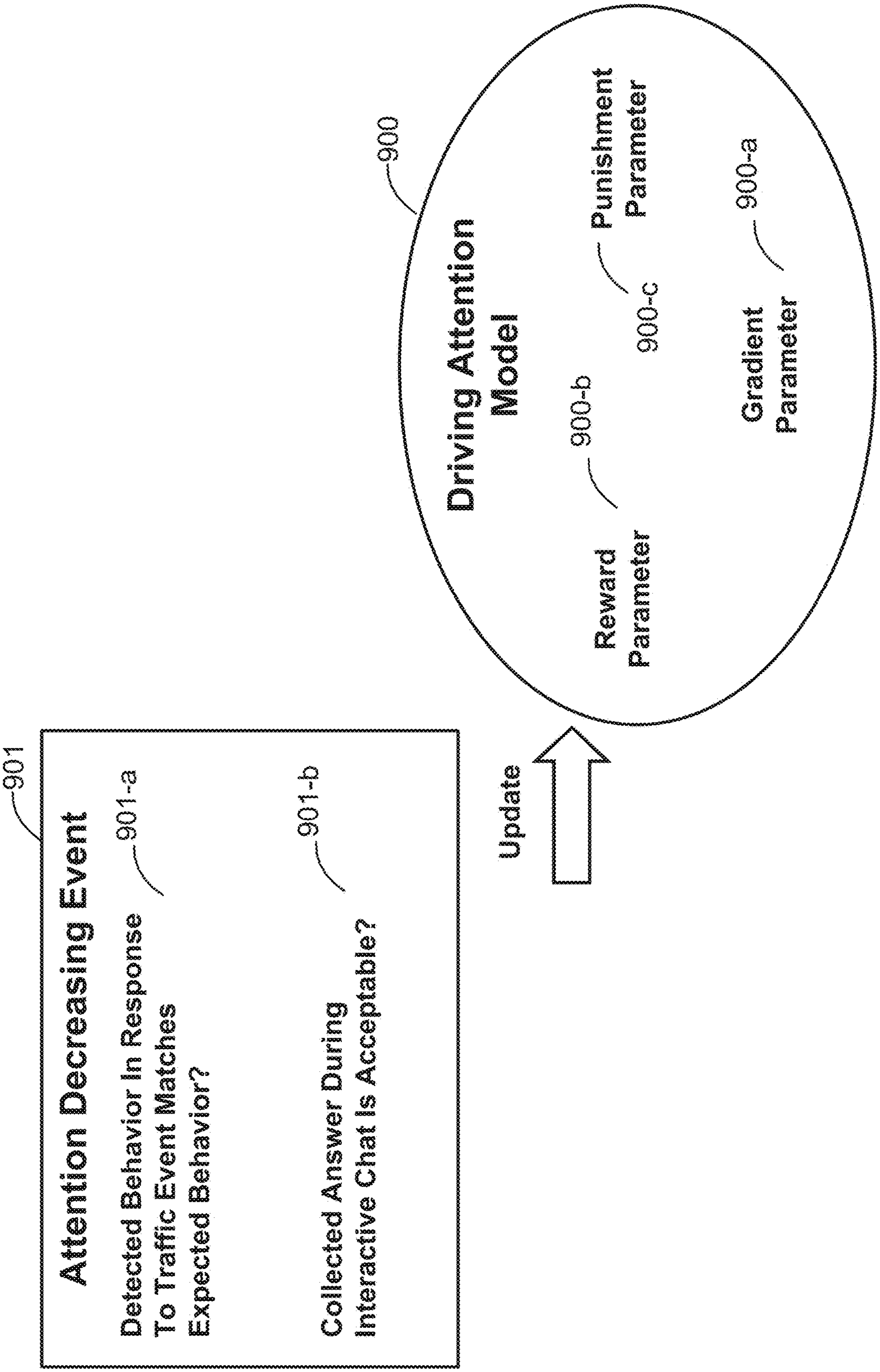
FIG. 9 shows an exemplary schematic diagram of updating the driving attention model based on attention decreasing events detected during a driving task according to an embodiment of the present disclosure.

FIG. 9 shows an exemplary schematic diagram of updating the driving attention model based on attention decreasing events detected during a driving task according to an embodiment of the present disclosure.

As shown in FIG. 9, the driving attention model 900 specific to a driver can be updated based on the attention decreasing events 901 detected for the driver's past driving tasks. It should be noted that the driving attention model 900 can be a same or different model with respect to the driving attention model 700 of FIG. 7.

In particular, the parameters of the driving attention model 900 can be updated based on a frequency of the attention decreasing events 901 detected during the past driving tasks, such as a frequency of the detected behavior of the driver not matching the expected behavior 901-*a*, and/or a frequency of the response time and/or response content of the answer during the interactive chat not satisfying an acceptable criterion 901-*b*. As illustrated examples, the parameters to be updated based on the frequency of the attention decreasing events may include those parameters characterizing the driving attention model, such as a gradient parameter 900-*a* indicative of a degradation of the attention level of the driver over time (e.g., gradient parameter for the degradation curve in FIG. 3, FIG. 4, and FIG. 8), a reward parameter indicative of an increase in the attention level in response to an attention increasing event of the driver (e.g., reward values as described in FIG. 3, FIG. 4, and FIG. 8), and a punishment parameter 900-*c* indicative of a decrease in the attention level in response to an attention decreasing event of the driver (e.g., punishment values as described in FIG. 3, FIG. 4, and FIG. 8), among other parameters.

For example, if the attention decreasing events occur frequently, the gradient parameter can be increased and the punishment parameter can also be increased. If the attention decreasing events occur less frequently, the gradient parameter can be decreased and the reward parameter can be increased. It should be noted that other adjustments to the parameters of the model can also be contemplated in the present disclosure.

According to embodiments of the present disclosure, the initial parameters of the driving attention model can be obtained based on statistical data regarding driving activities and theoretical research on the road safety, which can be directed to a variety of groups of drivers with different driving experiences and habits and also directed to a variety of different road conditions and geometry changes. Additionally, the initial parameters of the model (e.g., the gradients for the degradation curve, the reward parameter and punishment parameter) can be further updated based on personalized driving data of the driver, and thus can be customized to predict the attention level of that driver reliably and accurately.

It should be noted that the driving attention model can be various types of machine learning model, which can be updated based on the driving data of the driver and thus used as a personalized model of the driver. For example, the gradient parameter 900-*a*, the reward parameter 900-*b*, and the punishment parameter 900-*c* for a first driving attention model for a first driver can be different from those for a second driving attention model for a second driver, since the models are independently updated based on the driving data of their own drivers. Even for the same driver, the parameters can also be updated dynamically and change from time to time, which may be dependent on the drive data acquired for the user during a particular time duration.

Finally, it should be noted that the approach of driver attention monitoring can be implemented in various manners. For example, the driver attention monitoring can be implemented in a navigation application, in a vehicle component, and the like. In this case, the navigation application and/or vehicle component can be implemented as a standalone module and used to predict the driver attention and avoid the driver distraction effectively and accurately, thereby improving road safety.

Figure 10:
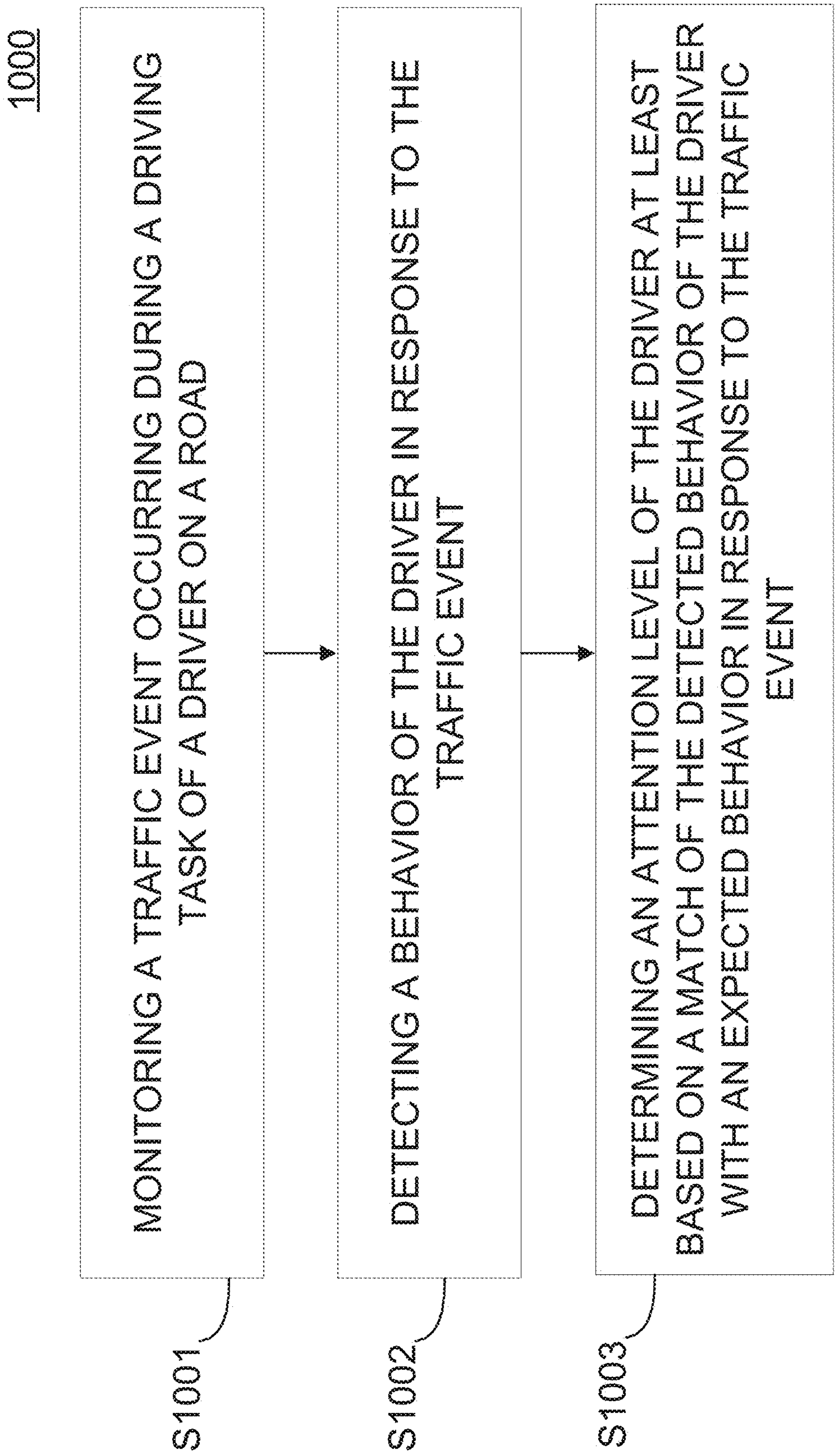
FIG. 10 shows a flowchart of a computer-implemented method of driver attention monitoring according to an embodiment of the present disclosure.

FIG. 10 shows a flowchart of a computer-implemented method 1000 of driver attention monitoring according to an embodiment of the present disclosure. The detailed description of method 1000 can refer to the content described in the above with respect to FIGS. 1-9. Each step of method 1000 can be performed by one or more processing units, such as central processing unit (CPU).

With reference to FIG. 10, method 1000 comprises steps S1001-S1003.

At step S1001, a traffic event occurring during a driving task of a driver on a road can be monitored. For example, the traffic event may be common traffic events occurring inside or outside the vehicle and requiring the driver's adequate attention and prompt responsive action, as described in the above.

At step S1002, a behavior of the driver in response to the traffic event can be detected. For example, the driver's behavior can be detected based on signals acquired from various sensors mounted on the vehicle platform, based on visual processing of the captured body movement of the driver, and the like.

At step S1003, an attention level of the driver can be determined at least based on a match of the detected behavior of the driver with an expected behavior in response to the traffic event. For example, the attention level of the driver is determined with the aid of a driving attention model specific to the driver. As another example, the determining of the attention level of the driver is further based on an explanation to the detected behavior provided by the driver, such as reasonable explanations provided during the interactive chat, as mentioned above.

In some examples, the attention level of the driver is determined based on an incremental value or a decremental value applied to a current attention level of the driver, wherein the incremental value or the decremental value is determined based on a match or mismatch of the detected behavior with the expected behavior.

Optionally, method 1000 can also comprise a step of initiating an interactive chat with the driver. According to embodiments of the present disclosure, the interactive chat can be initiated in response to the determined attention level of the driver falling below an attention threshold and/or a periodic timing for initiating the interactive chat having arrived.

In case that the interactive chat can be initiated, method 1000 can also comprise steps of acquiring an answer provided by the driver with respect to a question of the interactive chat; and updating the attention level of the driver based on a response time and/or response content of the answer provided by the driver.

According to embodiments of the present disclosure, the question of the interactive chat is generated with the aid of a language model based on a context of the driving task. In an example, the attention level of the driver is updated at least based on a match of the response content with an expected answer generated with aid of the LLM. In another example, the attention level of the driver is updated at least based on a semantic analysis of the response content in combination with the context and the generated question with the aid of the LLM. In yet another example, the question of the interactive chat is selected from a plurality of different question types based on a context of the driving task and/or a preference of the driver.

Optionally, method 1000 can also comprise a step of sending one or more control signals to one or more vehicle components for attention promotion in response to the attention level of the driver falling below an attention threshold.

In case that the attention level of the driver is determined with the aid of the driving attention model specific to the driver, the attention level of the driver can be determined further based on an elapsed time period of the driving task, one or more driver states of the driver and/or one or more road conditions of the road. For example, the one or more driver states can indicate one or more of an age, a gender, a driving experience and an emotional state of the drive, and the more road conditions can indicate one or more of a type, a geometry and a traffic density of the road. In this case, one or more of the elapsed time period of the driving task, the one or more driver states of the driver, the one or more road conditions of the road, the detected behavior in response to the detected traffic event, and the acquired answer during the interactive chat can be input to the driving attention model, in order to comprehensively evaluate the attention level of the driver during the driving task.

Additionally, the driving attention model can be updated such that the model is a personalized model for accurately predicting the driver's attention level. According to embodiments of the present disclosure, the driving attention model is updated based on a frequency of attention decreasing events (or equivalently, a frequency of attention increasing events) of the driver. In an example, the driving attention model is updated based on a frequency of the response time and/or response content of the answer not satisfying a predetermined condition. In another example, the driving attention model is updated based on a frequency of the detected behavior of the driver not matching the expected behavior.

In case that the driving attention model can be updated, the parameters characterizing the driving attention model, such as a gradient parameter indicative of a degradation of the attention level of the driver over time, a reward parameter indicative of an increase in the attention level in response to an attention increasing event of the driver, and a punishment parameter indicative of a decrease in the attention level in response to an attention decreasing event of the driver, can be updated based on the frequency of the attention decreasing events. For example, the frequency of the attention decreasing events may include the frequency of the response time and/or response content of the answer not satisfying a predetermined condition, and/or the frequency of the detected behavior of the driver not matching the expected behavior.

Optionally, method 1000 can also comprise steps of determining an occurrence of an attention decreasing event of the driver; and acquiring a facial feature and/or a body pose of the driver captured in the attention decreasing event. In this case, the driving attention model can be updated further based on the facial feature and/or the body pose such that the attention level of the driver is determined further based on subsequently captured facial features and/or body poses of the driver.

Figure 11:
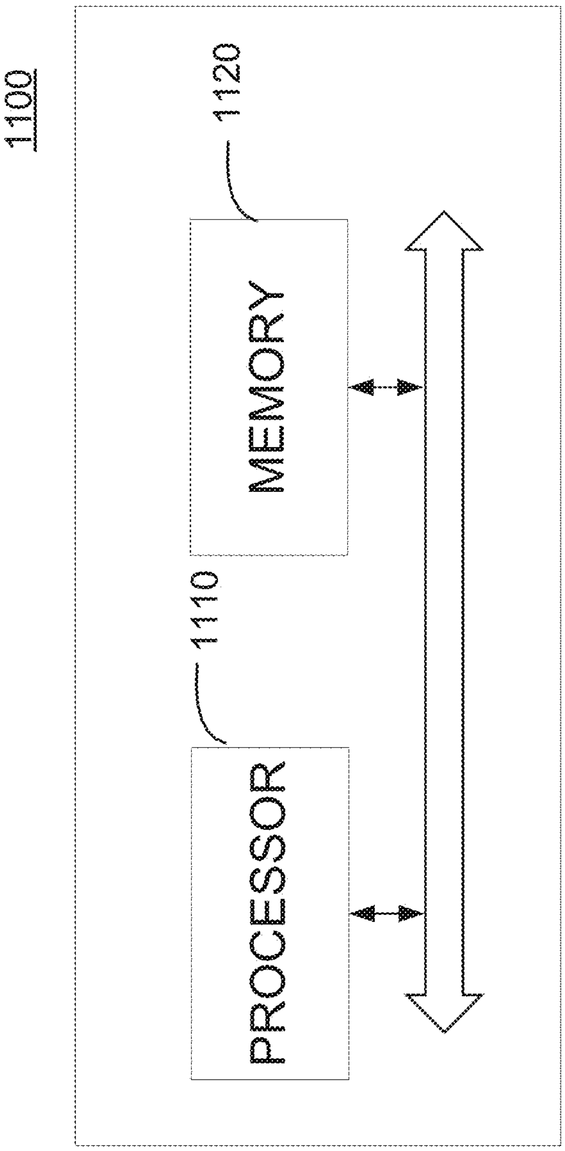
FIG. 11 shows a system of driver attention monitoring according to an embodiment of the present disclosure.

FIG. 11 shows a system 1100 of driver attention monitoring according to an embodiment of the present disclosure. The system 1100 of driver attention monitoring comprises one or more processors 1110 and a memory 1120 coupled to at least one of the processors 1110 via a bus. A set of computer program instructions are stored in the memory 1120. When executed by at least one of the processors 1110, the set of computer program instructions perform following series of actions. A traffic event occurring during a driving task of a driver on a road can be monitored. A behavior of the driver in response to the traffic event can be detected. An attention level of the driver can be determined at least based on a match of the detected behavior of the driver with an expected behavior in response to the traffic event.

In an embodiment, the set of computer program instructions can further perform an action of initiating an interactive chat with the driver in response to the determined attention level of the driver falling below an attention threshold and/or a periodic timing for initiating the interactive chat having arrived.

In an embodiment, the set of computer program instructions can further perform actions of acquiring an answer provided by the driver with respect to a question of the interactive chat; and updating the attention level of the driver based on a response time and/or response content of the answer provided by the driver.

In an embodiment, the question of the interactive chat is generated with the aid of a language model based on a context of the driving task. In an example, the attention level of the driver is updated at least based on a match of the response content with an expected answer generated with aid of the language model, such as LLM. In another example, the attention level of the driver is updated at least based on a semantic analysis of the response content in combination with the context and the generated question with the aid of the language model.

In an embodiment, the question of the interactive chat is selected from a plurality of different question types based on a context of the driving task and/or a preference of the driver.

In an embodiment, the attention level is determined with the aid of a driving attention model specific to the driver, and wherein the driving attention model is updated based on a frequency of the response time and/or response content of the answer not satisfying a predetermined condition.

In an embodiment, determining the attention level of the driver is further based on an explanation to the detected behavior provided by the driver.

In an embodiment, determining the attention level of the driver is further based on an elapsed time period of the driving task, one or more driver states of the driver and/or one or more road conditions of the road.

In an embodiment, the one or more driver states indicate one or more of an age, a gender, a driving experience and an emotional state of the driver.

In an embodiment, the one or more road conditions indicate one or more of a type, a geometry and a traffic density of the road.

In an embodiment, the set of computer program instructions can further perform an action of sending one or more control signals to one or more vehicle components for attention promotion in response to the attention level of the driver falling below an attention threshold.

In an embodiment, the attention level is determined with the aid of a driving attention model specific to the driver, and wherein the driving attention model is updated based on a frequency of the detected behavior of the driver not matching the expected behavior.

In an embodiment, the driving attention model is characterized by at least one of a gradient parameter indicative of a degradation of the attention level of the driver over time, a reward parameter indicative of an increase in the attention level in response to an attention increasing event of the driver, and a punishment parameter indicative of a decrease in the attention level in response to an attention decreasing event of the driver. Accordingly, at least one of the gradient parameter, the reward parameter and the punishment parameter of the driving attention model is updated based on the frequency of the detected behavior of the driver not matching the expected behavior and/or the frequency of the response time and/or response content of the answer not satisfying the predetermined condition.

In an embodiment, the set of computer program instructions can further perform actions of determining an occurrence of an attention decreasing event of the driver; and acquiring a facial feature and/or a body pose of the driver captured in the attention decreasing event. In this case, the driving attention model is updated further based on the facial feature and/or the body pose such that the attention level of the driver is determined further based on subsequently captured facial features and/or body poses of the driver.

In an embodiment, the attention level of the driver is determined based on an incremental value or a decremental value applied to a current attention level of the driver, wherein the incremental value or the decremental value is determined based on a match or mismatch of the detected behavior with the expected behavior.

In addition, according to another embodiment of the present disclosure, a computer program product for monitoring driver attention is disclosed. As an example, the computer program product comprises a non-transitory computer readable storage medium having program instructions embodied therewith, and the program instructions are executable by a processor. When executed, the program instructions cause the processor to perform one or more of the above described procedures, and details are omitted herein for conciseness.

It should be noted that the processing of driver attention monitoring according to embodiments of this disclosure could be implemented in the computing environment of FIG. 1.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for monitoring driver attention, comprising:

monitoring, by one or more processing units, a traffic event occurring during a driving task of a driver on a road;

detecting, by one or more processing units, a behavior of the driver in response to the traffic event; and determining, by one or more processing units, an attention level of the driver at least based on a match of the detected behavior of the driver with an expected behavior in response to the traffic event and an explanation to the detected behavior provided by the driver.

2. The computer-implemented method of claim 1, further comprising:

initiating, by one or more processing units, an interactive chat with the driver in response to the determined attention level of the driver falling below an attention threshold and/or a periodic timing for initiating the interactive chat having arrived.

3. The computer-implemented method of claim 2, further comprising:

acquiring, by one or more processing units, an answer provided by the driver with respect to a question of the interactive chat; and updating, by one or more processing units, the attention level of the driver based on a response time and/or response content of the answer provided by the driver.

4. The computer-implemented method of claim 3, wherein the question of the interactive chat is generated with use of a language model based on a context of the driving task, and wherein the attention level of the driver is updated at least based on a match of the response content with an expected answer generated with the use of the language model.

5. The computer-implemented method of claim 3, wherein the question of the interactive chat is generated with use of a language model based on a context of the driving task, and wherein the attention level of the driver is updated at least based on a semantic analysis of the response content in combination with the context of the driving task and the generated question with the use of the language model.

6. The computer-implemented method of claim 3, wherein the question of the interactive chat is selected from a plurality of different question types based on a context of the driving task and/or a preference of the driver.

7. The computer-implemented method of claim 3, wherein the attention level is determined with use of a driving attention model specific to the driver, and wherein the driving attention model is updated based on a frequency of the response time and/or response content of the answer not satisfying a predetermined condition.

8. The computer-implemented method of claim 1, wherein determining the attention level of the driver is further based on an elapsed time period of the driving task, one or more driver states of the driver, and/or one or more road conditions of the road.

9. The computer-implemented method of claim 8, wherein the one or more driver states indicate one or more of an age, a gender, a driving experience and an emotional state of the driver.

10. The computer-implemented method of claim 8, wherein the one or more road conditions indicate one or more of a type, a geometry and a traffic density of the road.

11. The computer-implemented method of claim 1, further comprising:

sending, by one or more processing units, one or more control signals to one or more vehicle components for attention promotion in response to the attention level of the driver falling below an attention threshold.

12. The computer-implemented method of claim 1, wherein the attention level is determined with use of a driving attention model specific to the driver, and wherein the driving attention model is updated based on a frequency of the detected behavior of the driver not matching the expected behavior.

13. The computer-implemented method of claim 12, wherein the driving attention model is characterized by at least one of: a gradient parameter indicative of a degradation of the attention level of the driver over time, a reward parameter indicative of an increase in the attention level in response to an attention increasing event of the driver, and a punishment parameter indicative of a decrease in the attention level in response to an attention decreasing event of the driver, and wherein at least one of the gradient parameter, the reward parameter and the punishment parameter of the driving attention model is updated based on the frequency of the detected behavior of the driver not matching the expected behavior.

14. The computer-implemented method of claim 12, further comprising:

determining, by one or more processing units, an occurrence of an attention decreasing event of the driver; and acquiring, by one or more processing units, a facial feature and/or a body pose of the driver captured in the attention decreasing event, wherein the driving attention model is updated further based on the facial feature and/or the body pose such that the attention level of the driver is determined further based on subsequently captured facial features and/or body poses of the driver.

15. The computer-implemented method of claim 1, wherein the attention level of the driver is determined based on an incremental value or a decremental value applied to a current attention level of the driver, and wherein the incremental value or the decremental value is determined based on a match or mismatch of the detected behavior with the expected behavior.

16. A system for monitoring driver attention, comprising:

one or more processors;

a memory coupled to at least one of the processors; and a set of computer program instructions stored in the memory, which, when executed by at least one of the processors, perform actions of:

monitoring a traffic event occurring during a driving task of a driver on a road;

detecting a behavior of the driver in response to the traffic event; and determining an attention level of the driver at least based on a match of the detected behavior of the driver with an expected behavior in response to the traffic event and an explanation to the detected behavior provided by the driver.

17. The system of claim 16, wherein the set of computer program instructions, when executed by the at least one of the processors, further perform actions of:

initiating an interactive chat with the driver in response to the determined attention level of the driver falling below an attention threshold and/or a periodic timing for initiating the interactive chat having arrived.

18. The system of claim 17, wherein the set of computer program instructions, when executed by the at least one of the processors, further perform actions of:

acquiring an answer provided by the driver with respect to a question of the interactive chat; and updating the attention level of the driver based on a response time and/or response content of the answer provided by the driver.

19. A computer program product for monitoring driver attention, the computer program product comprising a non-transitory computer readable storage medium having program instructions embodied therewith, the program instructions executable by a processor to cause the processor to:

monitor a traffic event occurring during a driving task of a driver on a road;

detect a behavior of the driver in response to the traffic event; and determine an attention level of the driver at least based on a match of the detected behavior of the driver with an expected behavior in response to the traffic event and an explanation to the detected behavior provided by the driver.

* * * * *